US008568716B2

(12) United States Patent
Franano

(10) Patent No.: US 8,568,716 B2
(45) Date of Patent: *Oct. 29, 2013

(54) KIT COMPRISING ELASTASE

(75) Inventor: F. Nicholas Franano, Kansas City, MO (US)

(73) Assignee: Proteon Therapeutics, Inc., Waltham, MA (US)

(*) Notice: Subject to any disclaimer, the term of this patent is extended or adjusted under 35 U.S.C. 154(b) by 279 days.

This patent is subject to a terminal disclaimer.

(21) Appl. No.: 11/454,554

(22) Filed: Jun. 16, 2006

(65) Prior Publication Data

US 2007/0014782 A1  Jan. 18, 2007

Related U.S. Application Data

(62) Division of application No. 06/669,051, filed on Sep. 24, 2000, now Pat. No. 7,063,838.

(60) Provisional application No. 60/155,938, filed on Sep. 24, 1999.

(51) Int. Cl.

| | |
|---|---|
| *A61K 38/46* | (2006.01) |
| *A61K 38/48* | (2006.01) |
| *A61K 38/55* | (2006.01) |
| *A61K 35/39* | (2006.01) |
| *C12Q 1/34* | (2006.01) |
| *C12Q 1/37* | (2006.01) |
| *A61M 25/06* | (2006.01) |
| *A61M 29/02* | (2006.01) |
| *A61M 31/00* | (2006.01) |
| *A61M 25/085* | (2006.01) |
| *A61M 25/10* | (2013.01) |
| *A61M 29/00* | (2006.01) |

(52) U.S. Cl.
USPC .............. 424/94.64; 435/18; 435/23; 435/24; 435/975; 604/103.02; 604/507; 604/509

(58) Field of Classification Search
USPC ..................... 424/94.64; 435/18, 23, 24, 975; 604/103.02, 507, 509
See application file for complete search history.

(56) References Cited

U.S. PATENT DOCUMENTS

| | | | | |
|---|---|---|---|---|
| 73,402 A | * | 1/1868 | Sornborger | 604/187 |
| 4,636,195 A | | 1/1987 | Wolinsky et al. | 604/49 |
| 4,803,294 A | | 2/1989 | Mueller et al. | 560/54 |
| 4,968,614 A | | 11/1990 | Takiguchi et al. | 435/172.3 |
| 4,985,361 A | | 1/1991 | Takiguchi et al. | 435/218 |
| 5,041,091 A | | 8/1991 | Herring | 604/102 |
| 5,116,615 A | | 5/1992 | Gokcen et al. | 424/94.2 |
| 5,162,205 A | | 11/1992 | Takiguchi et al. | 435/68.1 |
| 5,212,068 A | | 5/1993 | Takiguchi et al. | 435/68.1 |
| 5,397,694 A | | 3/1995 | Atkinson et al. | 435/2 |
| 5,489,261 A | | 2/1996 | Franzblau et al. | 602/41 |
| 5,693,029 A | | 12/1997 | Leonhardt | |
| 5,710,035 A | | 1/1998 | Greene et al. | 435/218 |
| 5,713,863 A | | 2/1998 | Vigil et al. | |
| 5,834,449 A | | 11/1998 | Thompson et al. | 514/152 |
| 5,922,322 A | | 7/1999 | Bini | 424/94.67 |
| 5,944,710 A | | 8/1999 | Dev et al. | 435/173.6 |
| 6,074,659 A | | 6/2000 | Kunz et al. | 424/423 |
| 6,074,664 A | | 6/2000 | Roreger et al. | 424/443 |
| 6,143,744 A | | 11/2000 | Broka et al. | 514/238.2 |
| 6,210,392 B1 | * | 4/2001 | Vigil et al. | 604/507 |
| 6,347,247 B1 | | 2/2002 | Dev et al. | 607/2 |

FOREIGN PATENT DOCUMENTS

| | | |
|---|---|---|
| EP | 1 923 068 B1 | 6/2011 |
| WO | 90/08555 A1 | 8/1990 |
| WO | WO 96/18725 | 6/1996 |
| WO | 96/36227 A1 | 11/1996 |

OTHER PUBLICATIONS

Wikipedia, http://en.wikipedia.org/wiki/Catheter, Printed Sep. 14, 2008.*
Sigma Catalog. 1997. Elastase E-1250, p. 433.*
Kovács et al. 1959. The properties and Therapeutic uses of Elastase. Therapia Hungarica, English Translation, vol. 7, pp. 39-44.*
Abbruzzese, T. et al., *Surgery*, 124:328-335 (1998).
Altes et al., *AJR*. 174:349-354 (Feb. 2000).
Anidjar, S. et al., *Ann. Vasc. Surg.*, 8(2):127-136 (1994).
Anidjar, S. et al., *Journal of Vascular Surgery*, 16(2):139-147 (1992).
Anidjar, S. et al., *Circulation* 82(3):973-981 (1990).
Arakawa, M. et al., *Japanese Journal of Clinical and Experimental Medicine*, 62(3):1-15 (1985).
Carsten, C. et al., *Journal of Vascular Surgery*, 33(6):1255-1262 (2001).
Cloft, H. et al., *Radiology*, 213:223-228 (1999).
Curci, J. et al. *Journal of Vascular Surgery*, 385 (Feb. 1999).
Dobrin, P. et al., *Surgery*, 104(3):568-571 (1988).
Dobrin, P. et al., *Arch. Surg.*, 119:405-409 (1984).
Erlendsson, L. et al., *Comparative Biochemistry and Physiology*, Part B, 120:549-557 (1998).
Fujiwara, N. et al., *Am. J. Neuroradiol.* 22:698-703 (2001).
Geary, R. et al., *Journal of Vascular Surgery*, 27(1):96-108 (1998).
Hammond, G. et al., *J. Surgical Research*, 12(4):313-317 (1972).
Hasegawa, M. *Biorheology*, 20(5):531-545 (1983).

(Continued)

*Primary Examiner* — Jon P Weber
*Assistant Examiner* — Kailash C Srivastava
(74) *Attorney, Agent, or Firm* — Fried, Frank, Harris, Shriver & Jacobson LLP

(57) ABSTRACT

The invention provides methods for treating an obstructed biological conduit that include administering to the conduit an agent that can degrade extracellular matrix of obstructing tissue. Particular methods include delivery of an enzyme or a mixture of several enzymes to the area or region of obstruction wherein the enzyme(s) have the capability to degrade extracellular matrix components within the obstruction thereby restoring the normal flow of transported fluid through the conduit. The invention also includes prophylactically dilating a section of conduit to minimize the risk of obstruction formation.

14 Claims, 5 Drawing Sheets

(56) References Cited

OTHER PUBLICATIONS

Johnson, MS et al. The Porcine Hemodialysis Access Model, *Journal of Vascular and Interventional Radiology* 2001;12(8):969-977.
Kabemba, J. et al., *Surgery*, 73(3):438-443 (1973).
Kitoh, T. et al., American Journal of Physiology, 265(1 Pt 2):H273-80 (1993).
Lafont, A. et al., *Seminars in Interventional Cardiology*, 2:177-182 (1997).
Maillard, L. et al., *Gene Therapy*, 5:1023-1030 (1998).
Matsushita, M. et al., *Eur. Surg. Res.* 31:305-313 (1999).
Miskolczi, L. et al., *Neurosurgery*, 41(1):220-229 (1997).
Miskolczi, L. et al., *Neurosurgery*, 43(3):595-600 (1998).
Moore, G. et al., *Journal of Vascular Surgery*, 2993):522-532 (1999).
Muto, Y. et al., *Japan J. Surg.*, 16(3):225-230 (1986).
Ooyama, T. et al., *The Molecular Biology and Pathology of Elastic Tissues*, Wiley, Chichester (Ciba Foundation Symposium 192), pp. 307-320 (1995).
Origuchi, N. et al., *International Angiology*, 17(2):113-119 (1998).
Osman, M. et al., *J. Lab Clin. Med.*, 105(2):254-258 (1985).
Petrinec, D. et al. *Journal of Vascular Surgery*, 23(2):336-46 (1996).
Senior, R. et al. *J. Biol. Chem.* 266(12):7870-7875 (1991).
Singleton, P. et al., *Dictionary of Microbiology and Molecular Biology* (2nd ed. 1987, reprinted 1991), John Wiley and Sons, p. 320.
Strauss, BH et al. *Extracellular Matrix Remodeling After Balloon Angioplasty Injury in a Rabbit Model of Restenosis Circulation Research.*, 75(4):650-658 (1994).
Strindberg, G. et al., *Journal of Investigative Surgery*, 11(3):185-197 (1998).
White, J. et al., *Journal of Vascular Surgery*, 17(2):371-381 (1993).
White, J. *Journal of Vascular Surgery*, 20(1):153-155 (1994).
White, J.V. et al., *Ann. NY Acad. Sci.* 800:97-120 (Nov. 18, 1996).
Wilensky, RL et al., *Circulation*; 92(10):2995-3005 (1995).
Dobrin & Mrkvicka, *Cardiovas. Surg.*, 2(4): 484-488 (1994).
Trubel et al., *Eur J. Vasc. Endovasc. Surg.*, 10: 415-423 (1995).

Chernoyarova, O.D. and Podol'Skii, A.E. Mechanism of action of active elastase on pancreatic tissue. Bulletin of Experimental Biology and Medicine 78: 1340-1342 (1974).
Restriction Requirement mailed May 11, 2009 in U.S. Appl. No. 10/546,523.
Fujioka et al., Effect of Elastase on Primary Graft Patency after Femoralpopliteal Arterial Bypass for Arteriosclerosis Obliterans: A Randomized, Controlled Study. International Surgery 82: 94-97 (1997).
O-Hara et al., Effect of Pancreatopeptidase E (Elastase) on the Suppression of Intimal Fibrous Proliferation After Arterial Reconstruction in High Cholesterol Fed Rabbits. Journal of Cardiovascular Surgery 29: 268-276 (1988).
Hayashi et al. Effects of elastase on the stiffness and elastic properties of arterial walls in cholesterol-fed rabbits. Atherosclerosis 66:259-267 (1987).
Saeki et al. Antiatheromatous properties of elastase in cholesterol-fed rabbits and ex vivo suppressive effect of elastase on smooth muscle cell proliferation in the presence of hypercholesterolemia. Acta Pathol. Jpn. 37(9): 123-1432 (1987).
Toda et al. Promotive effect of elastase on regression of aortic atherosclerosis in cholesterol-fed quails. Exp. Pathol. 36:201-209 (1989).
Lewis et al., Pancreatic Elastase: Purification, Properties, and Function. Journal of Biological Chemistry 222: 705-720 (1956).
Mitchel et al., Enhanced Local Intracoronary Delivery of Heparin with the Infiltrator Catheter: A Comparative Study. Journal of Invasive Cardiology 11: 463-470 (Aug. 1999).
Akimoto. The Effect of Pancreatopeptidase E (Elastase) on Anastomotic Intimal Thickness in Two Types of Vascular Prosthesis. Surgery Today 25:1027-1033 (1995).
Allaire et al. Local Overexpression of TIMP-1 Prevents Aortic Aneurysm Degeneration and Rupture in a Rat Model. J. Clin. Invest. 102:1413-1420 (1998).
Kerenyi et al. Local Enzymatic Treatment of Atherosclerotic Plaques, Exp. and Molec. Path. 49:330-338 (1988).

\* cited by examiner

STRICTURE

KIT COMPRISING ELASTASE

This application is a divisional of U.S. application Ser. No. 09/669,051, filed Sep. 24, 2000, now U.S. Pat. No. 7,063,838 B1 issued on Jun. 20, 2006, which claims the benefit of U.S. Provisional Application Ser. No. 60/155,938, filed Sep. 24, 1999, each of which is incorporated by reference herein in its entirety.

STATEMENT REGARDING GOVERNMENT RIGHTS

This invention was made with government support under grant no. HL07712-07 awarded by the National Institutes of Health. The government has certain rights in the invention.

BACKGROUND OF THE INVENTION

1. Field of the Invention

The present invention relates to methods of opening obstructed biological conduits. Preferred methods of the invention include methods and systems for opening obstructed biological conduits using local delivery of a therapeutic agent, particularly a protease, to lyse the extracellular matrix of the obstructing tissue.

2. Background

Obstructions to biological conduits frequently result from trauma to the conduit which can result from transplant, graft or other surgical procedures wherein the extracellular matrix of the obstructing tissue largely comprises collagen. Balloon angioplasty is a common initial treatment for stenosis or stricture obstruction that yields excellent initial results (Pauletto, *Clinical Science*, (1994) 87:467-79). However, this dilation method does not remove the obstructing tissue.

It only stretches open the lumen, the trauma of which has been associated with the release of several potent cytokines and growth factors that can cause an injury which induces another round of cell proliferation, cell migration toward the lumen and synthesis of more extracellular matrix. Consequently, balloon angioplasty is associated with restenosis in nearly all patients (Pauletto, *Clinical Science*, (1994) 87:467-79). There is currently no treatment that can sustain patency over the long term.

The extracellular matrix, which holds a tissue together, is composed primarily of collagen, the major fibrous component of animal extracellular connective tissue (Krane, J. Investigative Dermatology (1982) 79:83s-86s; Shingleton, Biochem. Cell Biol., (1996) 74:759-75). The collagen molecule has a base unit of three stands of repeating amino acids coiled into a triple helix. These triple helix coils are then woven into a right-handed cable. As the collagen matures, cross-links form between the chains and the collagen becomes progressively more insoluble and resistant to lysis. When properly formed, collagen has a greater tensile strength than steel. Not surprisingly, when the body builds new tissue collagen provides the extracellular structural framework such that the deposition of hard collagen in the lesion can result in duct obstruction.

Benign biliary stricture results in obstruction of the flow of bile from the liver and can result in jaundice and hepatic dysfunction. If untreated, biliary obstruction can result in hepatic failure and death. Biliary strictures can form after duct injury during cholecystectomy. They can also form at biliary anastomoses after liver transplantation and other biliary reconstructive surgeries (Vitale, Am. J. Surgery (1996) 171:553-7; Lilliemoe, Annals of Surgery (1997) 225).

Historically, benign biliary stricture has been treated surgically by removing the diseased duct segment and reconnecting the duct end-to-end, or connecting the duct to the bowel via a hepaticojejunostomy loop (Lilliemoe, Annals of Surgery (1997) 225). These long and difficult surgeries have significant morbidity and mortality due to bleeding, infection, biliary leak, and recurrent biliary obstruction at the anastomosis. Post-operative recovery takes weeks to months. More recently, minimally invasive treatments such as percutaneous balloon dilation have been utilized, yielding good initial biliary patency results (Vitale, Am. J. Surgery (1996) 171:553-7, Lilliemoe, Annals of Surgery (1997) 2250). However, balloon dilation causes a localized injury, inducing a healing response that often results in restenosis (Pauletto, Clinical Science, (1994)87:467-79). Long-term stenting at the common bile duct with flexible biliary drainage catheters is another minimally invasive alternative to surgery (Vitale, Am. J. Surgery (1996) 171:553-7). However, these indwelling biliary drainage catheters often become infected, or clogged with debris, and must be changed frequently. At present, long-term treatment of biliary stricture remains a difficult clinical problem.

Patients with chronic, end-stage renal failure may require replacement of their kidney function in order to survive. In the United States, long-term hemodialysis is the most common treatment method for end stage chronic renal failure. In 1993, more than 130,000 patients underwent long term hemodialysis (Gaylord, J. Vascular and Interventional Radiology (1993) 4:103-7); more than 80% of these patients implement hemodialysis through the use of a synthetic arteriovenous graft (Windus, Am. J. Kidney Diseases (1993) 21:457-71). In a majority of these patients, the graft consists of a 6 mm Gore-Tex tube that is surgically implanted between an artery and a vein, usually in the forearm or upper arm. This high flow conduit can then be accessed with needles for hemodialysis sessions.

Nearly all hemodialysis grafts fail, usually within two years, and a new graft must be created surgically to maintain hemodialysis. These patients face repeated interruption of hemodialysis, and multiple hospitalizations for radiological and surgical procedures. Since each surgical graft revision consumes more available vein, eventually they are at risk for mortality from lack of sites for hemodialysis access. One estimate placed the cost of graft placement, hemodialysis, treatment of complications, placement of venous catheters, hospitalization costs, and time away from work at as much as $500 million, in 1990 alone (Windus, *Am. J. Kidney Diseases* (1993) 21:457-71).

The most frequent cause of hemodialysis graft failure is thrombosis, which is often due to development of a stenosis in the vein just downstream from the graft-vein anastomosis (Safa, *Radiology* (1996) 199:653-7. Histologic analysis of the stenosis reveals a firm, pale, relatively homogeneous lesion interposed between the intimal and medial layers of the vein which thickens the vessel wall and narrows the lumen (Swedberg, *Circulation* (1989) 80:1726-36). This lesion, which has been given the name intimal hyperplasia is composed of vascular smooth muscle cells surrounded by an extensive extracellular collagen matrix (Swedberg, *Circulation* (1989) 80:1726-36; Trerotola, *J. Vascular and Interventional Radiology* (1995) 6:387-96). Balloon angioplasty is the most common initial treatment for stenosis of hemodialysis grafts and yields excellent initial patency results (Safa, *Radiology* (1996) 199:653-7). However, this purely mechanical method of stretching open the stenosis causes an injury which induces another round of cell proliferation, cell migration toward the lumen and synthesis of more extracellular matrix. Consequently, balloon angioplasty is associated with restenosis in nearly all patients (Safa, *Radiology* (1996) 199:653-7). There is currently no treatment which can sustain the patency of synthetic arteriovenous hemodialysis grafts over the long term.

Intimal hyperplasia research has focused largely on the cellular component of the lesion. The use of radiation and pharmaceutical agents to inhibit cell proliferation and migration are active areas of research (Hirai, *ACTA Radiologica* (1996) 37:229-33; Reimers, *J. Invasive Cardiology* (1998) 10:323-31; Choi, *J. Vascular Surgery* (1994) 19:125-34). To date, the results of these studies have been equivocal, and none of these new treatments has gained wide clinical acceptance. This matrix is composed predominantly of collagen and previous work in animals has demonstrated that systemic inhibition of collagen synthesis decreases the production of intimal hyperplasia (Choi, *Archives of Surgery* (1995) 130: 257-261).

During normal tissue growth and remodeling, existing collagen matrices must be removed or modified. This collagen remodeling is carried out by macrophages and fibroblasts, two cell types which secrete a distinct class of proteases called "collagenases" (Swedberg, *Circulation* (1989) 80:1726-36; Trerotola, *J. Vascular and Interventional Radiology* (1995) 6:387-96; Hirai, *ACTA Radiologica* (1996) 37:229-33). These collagenases rapidly degrade insoluble collagen fibrils to small, soluble peptide fragments, which are carried away from the site by the flow of blood and lymph.

See also U.S. Pat. Nos. 5,981,568; 5,409,926; and 6,074,659.

It thus would be desirable to provide new methods to relieve obstructions blocking flow through biological conduits.

SUMMARY OF THE INVENTION

I have now found new methods and systems for relieving an obstruction in a biological conduit, e.g. mammalian vasculature. Methods of the invention include administration to an obstruction site of a therapeutic agent that can preferably degrade (in vivo) the extracellular matrix of the obstructing tissue, particularly collagen and/or elastin. Preferred methods of the invention include administration to an obstruction of an enzyme or a mixture of enzymes that are capable of degrading key extracellular matrix components (including collagen and/or elastin) resulting in the solubilization or other removal of the obstructing tissue.

Methods and systems of the invention can be applied to a variety of specific therapies. For example, methods of the invention include treatment of biliary stricture with the use of exogenous collagenase, elastase or other agent, whereby an enzyme composition comprising collagenase, elastase or other agent is directly administered to or into (such as by catheter injection) the wall of the lesion or other obstruction. The enzyme(s) dissolves the collagen and/or elastin in the extracellular matrix, resulting in the solubilization of fibrous tissue from the duct wall near the lumen, and a return of duct flow or opening.

Methods of the invention also include pretreating an obstruction (e.g. in a mammalian duct) with collagenase, elastase or other agent to facilitate dilation such that if treatment under enzymatic degradation conditions alone is insufficient to reopen a conduit, then conventional treatment with e.g. balloon dilation is still an option. It has been found that enzymatic degradation pre-treatment in accordance with the invention can improve the outcome of balloon dilation since enzyme treatment partially digests the collagen fibrils. There-fore, the overall effect will be a softening of the remaining tissue. The softened tissue is more amenable to balloon dilation at lower pressures, resulting in less mechanical trauma to the duct during dilation.

Preferably, the therapeutic agent is delivered proximately to a targeted site, e.g. by injection, catheter delivery or the like.

A variety of therapeutic agents may be employed in the methods of the invention. Suitable therapeutic agents for use in the methods and systems of the invention can be readily identified, e.g. simply by testing a candidate agent to determine if it reduces an undesired vasculature obstruction in a mammal, particularly a coronary obstruction in a mammalian heart. Preferred therapeutic agents comprise one or more peptide bonds (i.e a peptidic agent), and typically contain at least 2, 3, 4, 5, 6, 7, 8, 9, or 10 or more amino acids, preferably one or more of the natural amino acids. Preferred therapeutic agents include large molecules, e.g. compounds having a molecular weight of at least about 1,000, 2,000, 5,000 or 10,000 kD, or even at least about 20,000, 30,000, 40,000, 50,000, 60,000, 70,000, 80,000, 90,000 or 100,000 kD.

Specifically preferred therapeutic agents for use in the methods and systems of the invention include proteases and other enzymes e.g. a collagenase such as Clostridial collagenase, a proteolytic enzyme that dissolves collagen, and/or an elastase such as a pancreatic elastase, a proteolytic enzyme that dissolves elastin. Preferred delivery of collagenase and other therapeutic agents of the invention include directly injecting the agent into the target lesion or other obstruction. Preferably, a homogeneous distribution of a therapeutic enzyme or enzyme mixture is administered to a target site with a drug delivery catheter. The therapeutic agent can then dissolve the key extracellular collagen components necessary to solubilize the obstructing tissue from the vessel wall near the lumen.

Treatment methods of the invention provide significant advantages over prior treatment methodologies. For example, enzymatic degradation of one or more key components of the extracellular matrix gently removes the tissue obstructing the lumen. Additionally, collagenolysis or other therapeutic administration is relatively atraumatic. Moreover, collagenase also can liberate intact, viable cells from tissue. Therefore, treatment methods of the invention can remove both the source of mechanical obstruction and a source of cytokines and growth factors, which stimulate restenosis.

A single or combination of more than one distinct therapeutic agents may be administered in a particular therapeutic application. In this regard, a particular treatment protocol can be optimized by selection of an optimal therapeutic agent, or optimal "cocktail" of multiple therapeutic agents. Such optimal agent(s) for a specific treatment method can be readily identified by routine procedures, e.g. testing selected therapeutic agents and combinations thereof in in vivo or in vitro assays.

In another aspect of the invention, treatment compositions and treatment kits are provided. More particularly, treatment compositions of the invention preferably contain one or more enzymatic agents such as collagenase preferably admixed with a pharmaceutically acceptable carrier. Such compositions can be suitable packaged in conjunction with an appropriate delivery tool such as an injection syringe or a delivery catheter. The delivery device and/or treatment solution are preferably packaged in sterile condition. The delivery device and treatment composition can be packaged separately or in combination, more typically in combination. The delivery device preferably is adapted for in situ, preferably localized, delivery of the therapeutic agent directly into the targeted biological conduit obstruction.

Typical subjects for treatment in accordance with the invention include mammals, particularly primates, especially humans. Other subjects may be treated in accordance with the invention such as domesticated animals, e.g. pets such as dogs, cats and the like, and horses and livestock animals such as cattle, pigs, sheep and the like. Subjects that may be treated in accordance with the invention include those mammals suffering from or susceptible to biliary stricture including benign biliary stricture, stenosis of hemodialysis graft, intimal hyperplasia, and/or coronary obstruction, and the like. As discussed above, methods of the invention may be administered as a pre-treatment protocol before another therapeutic regime such as a balloon angioplasty; during the course of another therapeutic regime, e.g. where a therapeutic composition of the invention is administered during the course of an angioplasty or other procedure; or after another treatment regime, e.g. where a therapeutic composition of the invention is administered after an angioplasty or administration of other therapeutic agents.

Other aspects of the invention are disclosed infra.

DETAILED DESCRIPTION OF THE INVENTION

Figure 1:
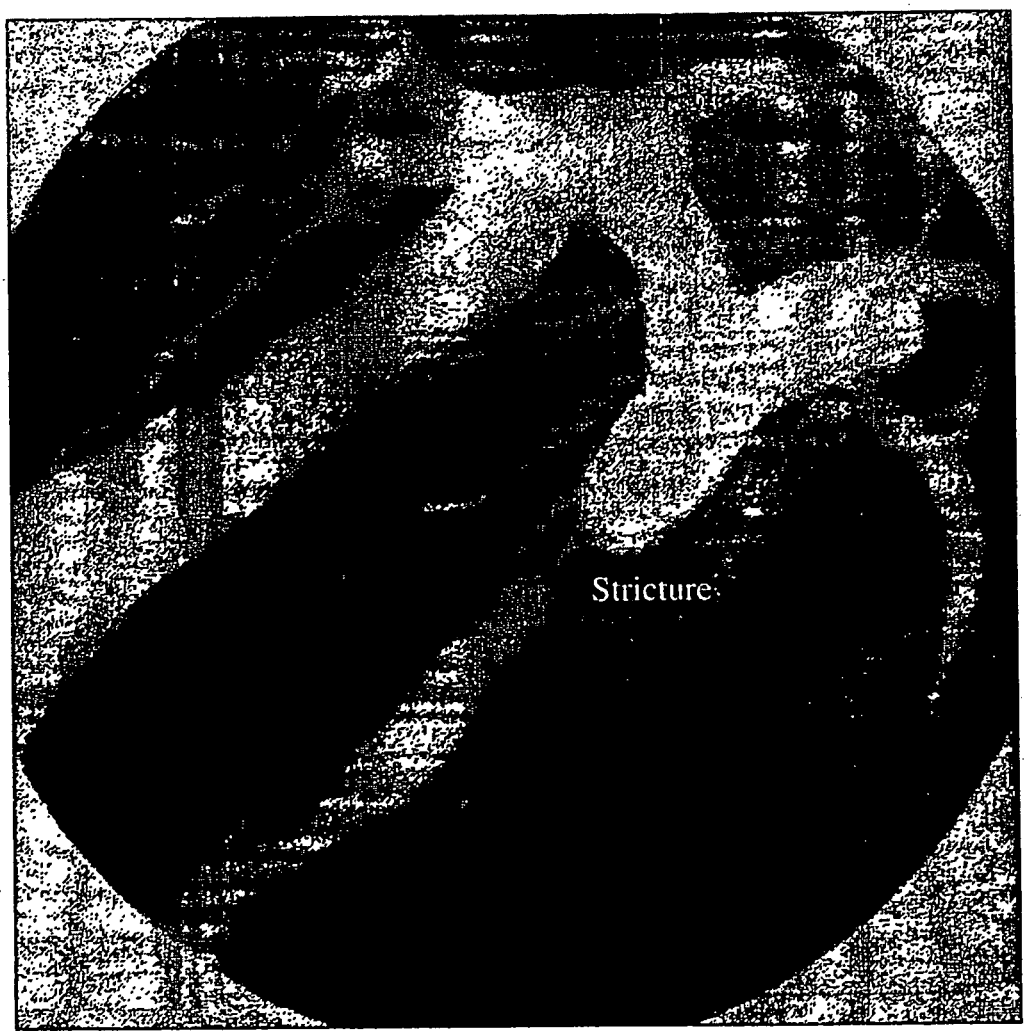
FIG. 1 shows a common bile duct in a dog with a high grade stricture.

The present invention provides methods of introducing a therapeutic agent that is capable of degrading an extracellular matrix component to thereby facilitate the reopening of a constricted biological conduit. In particular, the invention provides for introduction to an obstructed biological conduit of a therapeutic agent that degrades collagen and/or elastin. The present invention further provides methods of dilating a biological conduit by introducing a therapeutic agent into a biological conduit, preferably an isolated segment of the conduit.

In one embodiment of the present invention, the degradation of a stricture, lesion or other obstruction is accomplished by introducing one or more therapeutic agents that are capable of degrading one or more extracellular matrix components thereby facilitating the reopening of the constricted segment of the conduit. Major structural components of the extracellular matrix include collagen and elastin.

Preferred therapeutic agents for use in accordance with the invention are able to interact with and degrade either one or both of collagen and elastin.

As discussed above, a variety of compositions may be used in the methods and systems of the invention. Preferred therapeutic compositions comprise one or more agents that can solubilize or otherwise degrade collagen or elastin in vivo. Suitable therapeutic agents can be readily identified by simple testing, e.g. in vitro testing of a candidate therapeutic compound relative to a control for the ability to solubilize or otherwise degrade collagen or elastin, e.g. at least 10% more than a control.

More particularly, a candidate therapeutic compound can be identified in the following in vitro assay that includes steps 1) and 2):

1) contacting comparable mammalian tissue samples with i) a candidate therapeutic agent and ii) a control (i.e. vehicle carrier without added candidate agent), suitably with a 0.1 mg of the candidate agent contacted to 0.5 ml of the tissue sample; and 2) detecting digestion of the tissue sample by the candidate agent relative to the control. Digestion can be suitably assessed e.g. by microscopic analysis. Tissue digestion is suitably carried out in a water bath at 37° C. Fresh pig tendon is suitably employed as a tissue sample. The tissue sample can be excised, trimmed, washed blotted dry and weighed, and individual tendon pieces suspended in 3.58 mg/ml HEPES buffer at neutral pH. See Example 1 which follows for a detailed discussion of this protocol. Such an in vitro protocol that contains steps 1) and 2) is referred to herein as a "standard in vitro tissue digestion assay" or other similar phrase.

Preferred therapeutic agents for use in accordance with the invention include those that exhibit digestion activity in such a standard in vitro tissue digestion assay at least about 10 percent greater relative to a control, more preferably at least about 20% greater digestion activity relative to a control; still more preferably at least about 30%, 40%, 50%, 60%, 70%, 80%, 90% or 100% greater digestion activity relative to a control.

Appropriate therapeutic agents can comprise at least one and frequently several enzymes such that the therapeutic agent is capable of degrading both significant matrix components of tissue obstruction. Particularly preferable therapeutic agents will comprise either a collagenase or elastase or both. Specifically preferred are therapeutic agents comprising a highly purified, injectable collagenase preparation such as that produced from cultures of *Clostridium histolyticum* by BioSpecifics Technologies Corporation (Lynbrook, N.Y.). This enzyme preparation is composed of two similar but distinct collagenases. The Clostridial collagenases cleave all forms of collagen at multiple sites along the helix, rapidly converting insoluble collagen fibrils to small, soluble peptides. Also preferable are therapeutic agents comprising elastase, particularly pancreatic elastase, an enzyme capable of degrading elastin. Trypsin inhibitors also can be suitably employed as the therapeutic agent in the methods of the invention.

In a further aspect of the present invention, the methods further include means to prevent damage to tissue that is not associated with conduit obstruction. Preferred enzymes incorporated in the therapeutic agents are large (>100,000 kD) and diffuse slowly in the extracellular compartment after injection. Further, collagenases comprise a domain (in addition to the active site) which binds tightly to tissue. Consequently, these enzymes remain largely contained within collagen-rich target tissues after injection. Also, the enzyme's activity is quickly extinguished in the blood pool by circulating inhibitors. Therefore, injected collagenase, which diffuses from the interstitial compartment into the blood pool, will be rapidly inhibited, preventing systemic side effects.

Fragments of therapeutic agents also can be administered to a patient in accordance with the invention. For example, fragments of the above-mentioned collagenases and elastases can be administered to a patient provided such fragments provide the desired therapeutic effect, i.e. degradation of obstruction of a biological conduit. As referred to herein, a collagenase, elastase or other enzyme includes therapeutically effective fragments of such enzymes.

In certain preferred aspects of the invention, the therapeutic agent(s) that are administered to a patient are other than a cytostatic agent; cytoskeletal inhibitor; an aminoquinazolinone, particularly a 6-aminoquinazolinone; a vascular smooth muscle protein such as antibodies, growth hormones or cytokines.

In specific embodiments, the degradation of elastin, an extracellular matrix component that contributes to tissue elasticity, is not desirable. Therapeutic agents comprising only enzymes, which do not degrade elastin, such as collagenases, can be employed. Therefore, the elastic properties of the conduit wall will likely be preserved after treatment.

In a preferred aspect of the invention, a therapeutic agent comprising at least one enzyme capable of degrading elastin, collagen or both is delivered to the targeted obstruction site with a catheter. Preferred catheters are capable of directly localizing a therapeutic agent directly into the extracellular matrix of the obstruction. Particularly preferable catheters are capable of delivering accurate doses of the therapeutic agent with an even distribution over the entire obstructed area of the conduit. One particularly preferred example of a catheter for use in the method of the present invention is the Infiltrator® catheter produced by InterVentional Technologies Corporation (IVT) (San Diego, Calif.), which delivers a precisely controlled dosage of a drug directly into a selected segment of vessel wall (FIG. 1) (Reimers, J. Invasive Cardiology (1998) 10:323-331; Barath, *Catheterization and Cardiovascular Diagnosis* (1997) 41:333-41; Woessner, *Biochem. Cell Biol.* (1996) 74: 777-84). Using this preferred catheter a therapeutic agent can be delivered at low pressure via a series of miniaturized injector ports mounted on the balloon surface. When the positioning balloon is inflated, the injector ports extend and enter the vessel wall over the 360° surface of a 15 mm segment of vessel. Each injector port is les than 0.0035 inch in size. Drug delivery can be performed in less than 10 seconds, with microliter precision and minimal immediate drug washout. The injected drug is delivered homogeneously in the wall of the vessel or duct (FIG. 2). The triple lumen design provides independent channels for guidewire advancement, balloon inflation and drug delivery. Trauma associated with injector port penetration is minimal and the long-term histologic effects are negligible (Woessner, Biochem. *Cell Biol.* (1996) 74: 777-84). In addition, the device has been engineered such that the injector ports are recessed while maneuvering in the vessel. Additionally, the Infiltrator® catheter is capable of balloon inflation with sufficient force for angioplasty applications. The excellent control of drug delivery observed with Infiltratorg can be significant since preferred therapeutic agents of the present invention potentially can degrade collagen and/or elastin in nearly all forms of tissue in a non-specific manner.

In yet another embodiment of the present invention, a therapeutic dose is employed which will restore conduit flow while maintaining conduit wall integrity. Several parameters need to be defined to maximize method efficiency, including the amount of enzyme to be delivered, and the volume of enzyme solution to be injected so that the reopening of the conduit occurs with a single dose protocol. Ideally repeat or multiple dosing is reserved only for patients who have an incomplete response to the initial injection.

In regards to the volume of therapeutic agent solution delivered, preferably the conduit wall is not saturated completely, as this can lead to transmural digestion and conduit rupture. Instead, the optimal dose is determined by targeting the thickness of the wall (from the outside in) which needs to be removed in order to restore adequate flow, while leaving the remaining wall intact. An overly dilute solution will be ineffective at collagen lysis while an overly concentrated solution will have a higher diffusion gradient into the surrounding tissues, thereby increasing the risk of transmural digestion and rupture.

Collagenase doses are generally expressed as "units" of activity, instead of mass units. Individual lots of collagenase are evaluated for enzymatic activity using standardized assays and a specific activity (expressed in units/mg) of the lot is determined. BTC uses an assay that generates "ABC units" of activity. The specific activity of other collagenase preparations are sometimes expressed in the older "Mandel units". One ABC unit is roughly equivalent to two Mandel units.

Preferable doses and concentrations of enzyme solution are between 1000 and 20000 ABC units, more preferable are between 2500 and 10000 ABC units and enzyme doses of 5,000 ABC units in 0.5 ml of buffer are most preferred.

It will be appreciated that actual preferred dosage amounts of other therapeutic agents in a given therapy will vary according to e.g. the specific compound being utilized, the particular composition formulated, the mode of administration and characteristics of the subject, e.g. the species, sex, weight, general health and age of the subject. Optimal administration doses for a given protocol of administration can be readily ascertained by those skilled in the art using dosage determination tests, including those described above and in the examples which follow.

Therapeutic agents of the invention are suitably administered as a pharmaceutical composition with one or more suitable carriers. Therapeutic agents of the invention are typically formulated in injectable form, e.g. with the therapeutic agent dissolved in a suitable fluid carrier. See the examples which follow for preferred compositions.

As discussed above, the methods and systems of the invention can be employed to treat (including prophylactic treatment) a variety of diseases and disorders. In particular, methods and systems of the invention can be employed to relieve or otherwise treat a variety of lesions and other obstructions found in common bile ducts or vascular systems. Methods of the invention are also useful to relieve lesions and other obstructions in other biological conduits including e.g. ureter, pancreatic duct, bronchi, coronary and the like.

The invention also includes prophylactic-type treatment, e.g. methods to dilate a biological conduit whereby the increased conduit diameter obviates the potential of obstruction formation with a conduit. Temporary and partial degradation of the elastin component of a conduit wall reduces the elasticity of the conduit, thereby facilitating modifications of the size and shape of the conduit. Introducing a dose of therapeutic agent in accordance with the invention into the lumen of an isolated conduit or some section thereof results in complete or partial diffusion of the therapeutic agent into the wall of the isolated conduit during a specified period of time. Subsequent pressurization of the treated region, either while the region is still isolated or after removing the means of isolation, increases the lumen diameter by dilation. Regeneration of the conduit elastin framework results in a conduit with a larger lumen diameter without compromising the structural integrity.

Arteriovenous hemodialysis grafts are frequently placed in the arm of the patient such that blood can be withdrawn and purified blood returned through the graft. Frequently the lumenal diameter of the venous outflow is smaller than the graft lumenal diameter. Development of a stenosis due to intimal hyperplasia can further reduce the lumenal diameter of the venous outflow such that an insufficient volume of blood passes through the venous outflow. To prevent intimal hyperplasia and stenosis formation, dilating the venous outflow vein using the above described method of partially degrading the elastin component of the vascular wall downstream of the site of graft implantation such that the lumenal diameter of the venous outflow is similar to or larger than the diameter of the interposed loop graft reduces the likelihood of forming a stenosis due to intimal hyperplasia. Venous dilation can be performed either before or after interposing a graft between the artery and vein.

All documents mentioned herein are incorporated herein by reference. The present invention is further illustrated by the following non-limiting examples.

Example 1

Tissue Digestion Analysis

The protocol of the following example is a detailed description of a "standard in vitro tissue digestion assay" as referred to herein.

Figure 3:
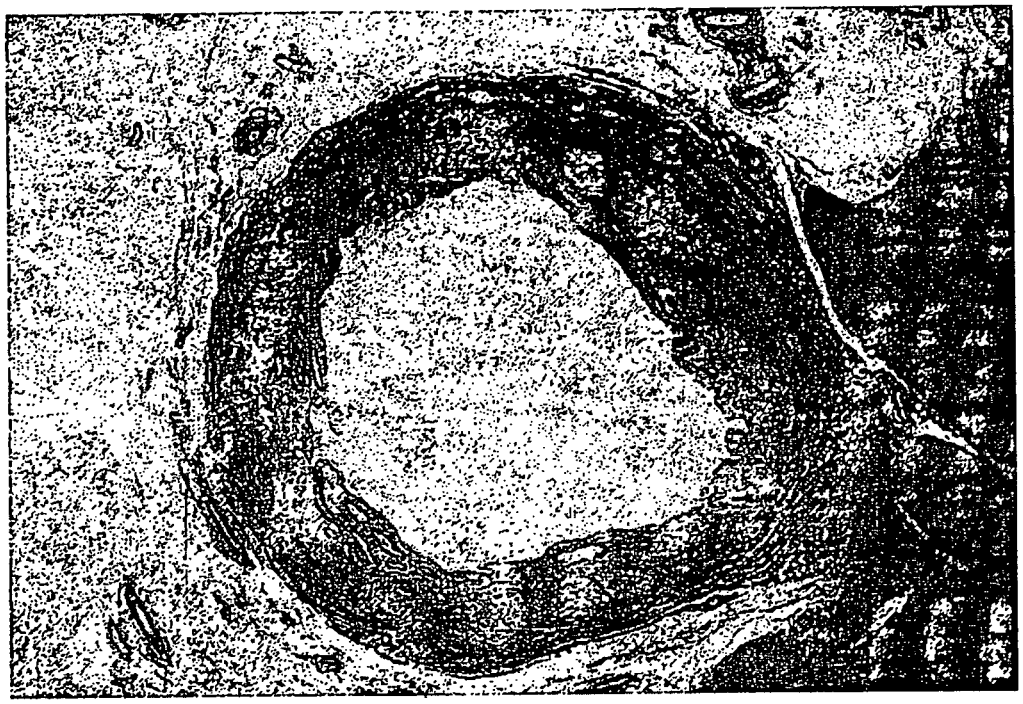
FIG. 3 is a histology picture of a normal common bile duct from a dog.

The rate of tissue digestion, which is composed mostly of collagen, by a mixture of collagenase and elastase, proteolytic enzymes with activity respectively against collagen and elastin, was determined. Trypsin inhibitor was added to negate the effect of any residual trypsin activity. Briefly, fresh pig tendon was excised, trimmed, washed, blotted dry and weighed. Individual tendon pieces were suspended in 3.58 mg/ml HEPES buffer at neutral pH and various concentrations of enzymes were added. Iodinated radiographic contrast was added in various concentrations to some of the enzyme solutions. The tissue digestion was carried out in a water bath at 37° C. At various time points, the tendon pieces were removed from the enzyme solution, washed, blotted dry and weighed. Each time point was derived from the average of three samples. The effect of enzyme concentration on tissue digestion rates was studied. As expected, increasing the concentration of enzymes in vitro increased the rate of tissue digestion (FIG. 3). Buffer alone had no effect on the tissue. Extrapolating digestion rates in vitro to an in vivo situation has proven difficult. For Dupuytren's contractures, the effective dose for transecting fibrous cords in vitro was 500 ABC units. However, the effective in vivo dose was 10,000 ABC units.

Figure 4:
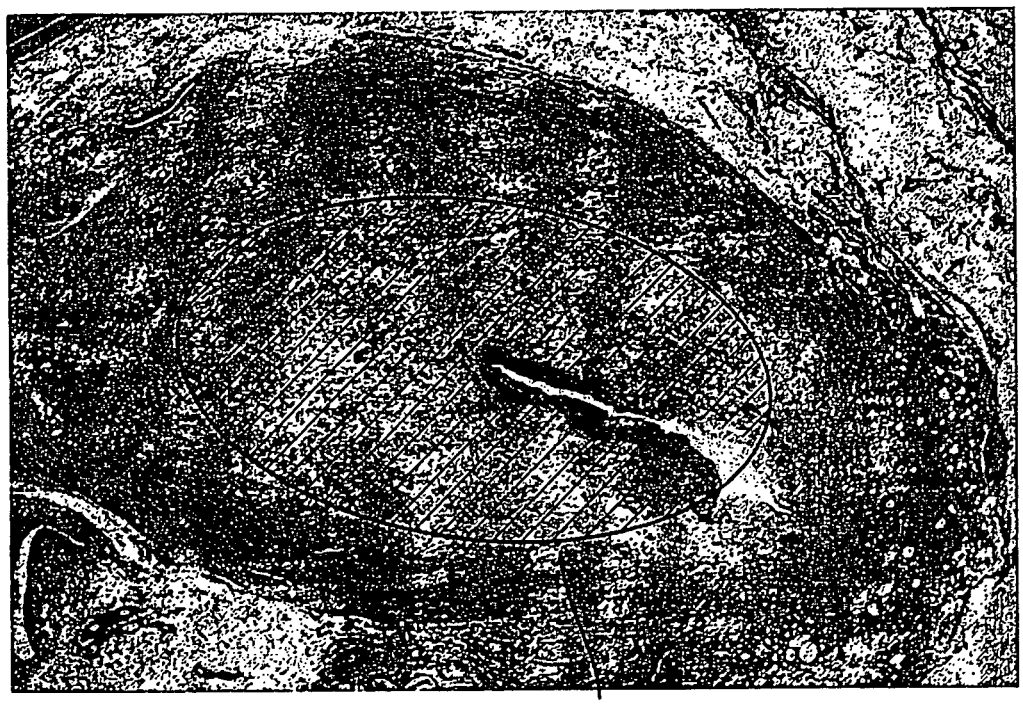
FIG. 4 is a histology picture of a common bile duct stricture from a dog with a high grade stricture before treatment.

The effect of iodinated radiographic contrast material on tissue digestion rates was also studied (FIG. 4). This study was performed to monitor enzyme delivery by mixing it with contrast prior to injection. These results demonstrate that Omnipaque 350 iodinated contrast material inhibits enzyme activity at radiographically visible (35%) concentrations, but not at lower (1-5%) concentrations (FIG. 4). Similar results were observed with Hypaque 60 contrast.

Example 2

Determining Dose Dependent in vitro Activity of a Therapeutic Agent Including Collagenase, Elastase, and a Trypsin Inhibitor The effect of enzyme concentration on tissue digestion rates was studied (FIG. 3). The "1×" tissue sample was treated with collagenase 156 Mandel units/ml+elastase 0.125 mg/ml+trypsin inhibitor 0.38 mg/ml. The "2×" sample was treated with collagenase 312 Mandel units/ml+elastase 0.25 mg/ml+trypsin inhibitor 0.76 mg/ml. The "5×" sample was treated with collagenase 780 Mandel units/ml+elastase 0.625 mg/ml+trypsin inhibitor 1.9 mg/ml. All digestion volumes were 0.5 ml. Increasing the concentration of enzymes in vitro increased the rate of tissue digestion (FIG. 3). Buffer alone had no effect on the tissue. An effective in vivo dose was found to be 10,000 ABC units.

Example 3

Determining the Effect of Iodinated Radiographic Contrast Material on Tissue Digestion Rates to Facilitate Monitoring Enzyme Delivery Prior to Injection of a Therapeutic Agent Comprising a Contrast Material into a Patient The "35% Omnipaque" tissue sample was treated with collagenase 156 Mandel units/ml+elastase 0.125 mg/ml+0.38 trypsin inhibitor with 35% Omnipaque 350 contrast (volume:volume). The "5% Omnipaque" sample was treated with collagenase 312 Mandel units/ml+elastase 0.25 mg/ml+0.76 trypsin inhibitor with 5% Omnipaque 350 (volume:volume). The "1% Omnipaque" sample was treated with collagenase 312 Mandel units/ml+elastase 0.25 mg/ml+0.76 trypsin inhibitor with 1% Omnipaque 350. All digestion volumes were 0.5 ml. These results demonstrate that Omnipaque 350 iodinated contrast material inhibits enzyme activity at radiographically visible (35%) concentrations, but not at lower (15%) concentrations (FIG. 4). Similar results were observed with Hypaque 60 contrast.

Example 4

Creating a Stricture in the Common Bile Duct of Dogs and Treatment of the Resulting Stricture with Transcatheter Intramural Collagenase Therapy Right subcostal laparotomy was performed in dogs to expose the gallbladder, which was then affixed to the anterior abdominal wall of 11 dogs (n=11). After 2 weeks, a single focal thermal injury was made in the common bile duct (CBD) using a catheter with an electrocoagulation tip placed through the gallbladder access. A 4.8 Fr biliary stent was placed to prevent complete duct occlusion in 7 animals. Stricture development was monitored with percutaneous cholangiography over five weeks. Collagenase was then directly infused into the wall of the strictured CBD using an Infiltrator drug delivery catheter (n=3). The Infiltrator has three arrays of microinjector needles mounted on a balloon which extend and enter the duct wall over the 360-degree surface. After treatment, internal plastic stents were placed in 2 animals. Explants of the CBD were obtained the following day. H&E, trichrome, and elastin staining were used for histopathologic analysis.

Figure 2:
FIG. 2 shows a common bile duct in a dog with a high grade stricture after treatment.
Figure 5:
FIG. 5 is a histology picture of a common bile duct stricture from a dog after treatment with collagenase wherein the arrows denote the outer limit of collagen breakdown.

CBD strictures were successfully created in 7/11 animals as determined by cholangiography (FIG. 1). Failures were due to gallbladder leak (n=2) and perforation at the site of thermal injury (n=2). Histologic analysis of an untreated stricture demonstrated a thickened wall with a circumferential network of collagen bundles and associated lumenal narrowing (FIG. 4). Strictures treated with collagenase demonstrated a circumferential lysis of collagen at the treatment site, with sparing of the normal duct, arteries and veins (FIGS. 2 and 5). All three animals developed bile leaks after treatment, two from the gallbladder access site and one from the treatment site. There was vascular congestion and inflammation in portions of the small bowel mucosa and peritoneum after treatment in all animals, to varying degrees.

Example 5

Relief of Strictures in the Common Bile Duct of a Patient

Figure 6:
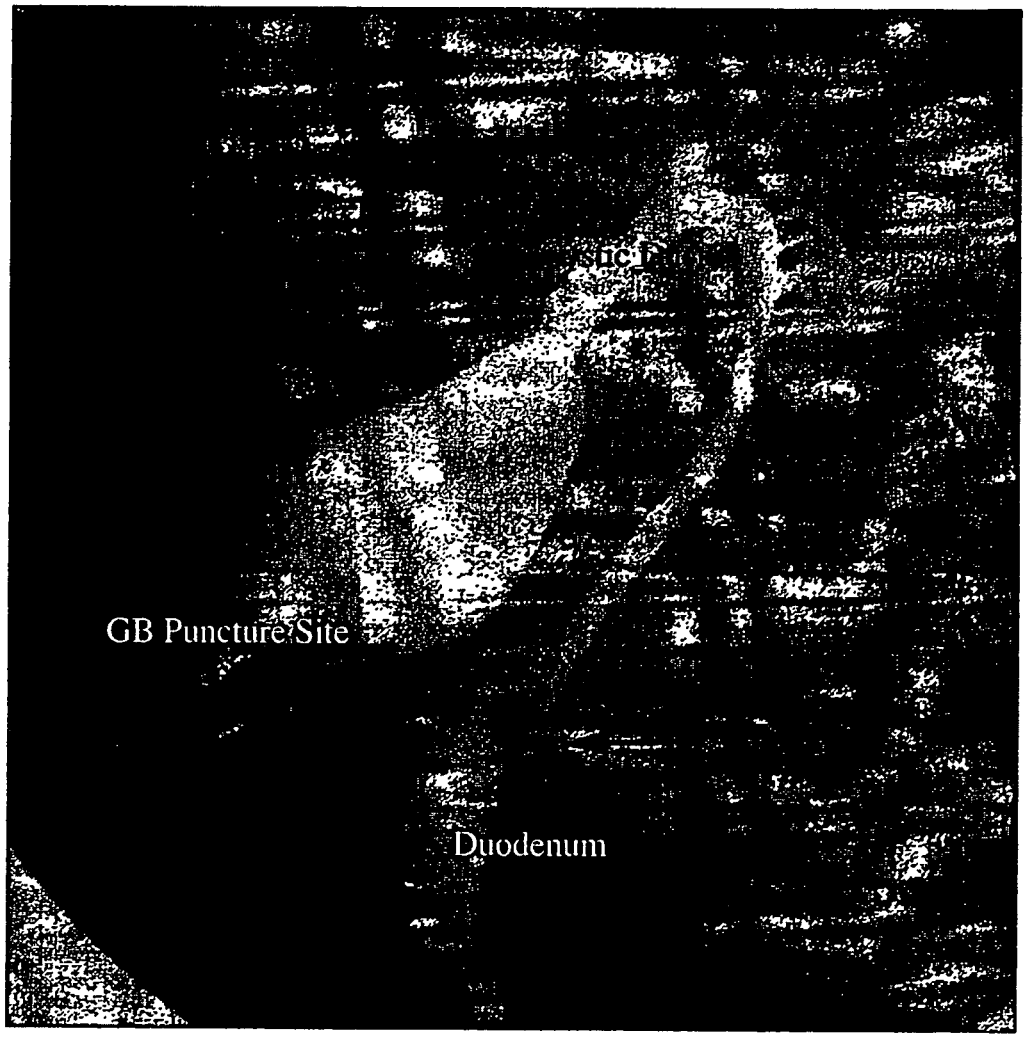
FIG. 6 shows a normal common bile duct in a dog.

A large dog was used as the patient such that under general anesthesia a cholecystostomy tract was created and the gallbladder was "tacked" to the abdominal wall with retention sutures. A cholangiogram was performed with Hypaque-60, using a marker catheter, in order to define the anatomy. Then, a flexible catheter with a bipolar electrode tip was constructed as previously described (Becker, *Radiology* (1988) 167:63-8). This catheter was inserted through the gallbladder (FIG. 5) and positioned with its "hot" tip (arrow) in the distal common bile duct such that the catheter was pulled back and the treatment was repeated until a 1.0 cm length of duct was injured (FIG. 6). Immediately after delivering the current there was a mild-moderate amount of smooth narrowing of the treated segment of duct (arrow), possibly due to spasm or edema. A pigtail nephrostomy drainage catheter was then inserted through the fresh cholecystotomy tract into the gallbladder. The distal end was closed with an IV cap and buried in the subcutaneous tissue. The surgical wounds were then closed in a two-layer fashion.

After 7 days, a follow-up cholangiogram was performed to evaluate the thermally induced stenosis. A 20 gauge needle was used to percutaneously access the drainage catheter through the IV cap. A cholangiogram was performed demonstrating moderate-marked dilation of the biliary tree (FIG. 1). There was a high-grade stricture of the mid common bile duct, where the thermal injury had been made.

Strictures are created in five large dogs using the methods described above and in Example 4. In addition, an objective measurement of biliary patency (the Whitaker study) is made of the common bile duct, both before and after making a stricture. The Whitaker study is performed by injecting normal saline through a catheter positioned in the common bile duct. Flow rates are increased and pressure measurements are taken until a peak pressure of 40 mmHg is reached.

The thermal lesions mature into fibrous strictures over a six week period. One animal is then sacrificed and a histologic assessment is made of the extrahepatic biliary tree. Samples are taken of the duct proximal to the lesion, the mid portion of the lesion (FIG. 4), the lesion edge, and the duct distal to the lesion. Assessments of 1) duct morphology. 2) cell type and number, 3) the extent and appearance of the extracellular matrix, and 4) extent of epithelialization are made. A second animal is sacrificed after an additional 6 weeks after thermal injury and a similar analysis carried out.

A cholangiogram is performed to visually assess the stricture (FIG. 1) and a whitaker test is also performed on the remaining 3 dogs. Then, the Infiltrator catheter is then deployed within the lesion and 0.5 mL of collagenase preparation (10,000 Units/ml) is injected into the wall of the lesion. On post-treatment day 1, a follow-up cholangiogram and Whitaker test are performed.

In cases where incomplete response is noted, a second treatment can be given and a second follow-up chlorangiogram and Whitaker test is performed the following day. Hepatic enzyme levels will be drawn to assess the effect of stricture and then treatment on hepatic function. Alternatively, incomplete response from collagenase can be followed up with subsequent angioplasty or a combined collagenase/angioplasty treatment.

After treatment with collagenase, a final cholangiogram is taken after 1 week (FIG. 2). At this time, the animal is sacrificed and the extrahepatic biliary tree harvested. Histologic assessments are made of the bile duct proximal to the treated lesion, the mid portion of the treated lesion (FIG. 5), the treated lesion edge, and the duct distal to the lesion. Assessments of 1) duct morphology, 2) cell type and number, 3) the extent and appearance of the extracellular matrix, and 4) extent of epithelialization were made. FIG. 5 is a histology image of a common bile duct stricture after treatment. The arrows denote the outer limit of collagen breakdown. The histological examination of the treated common bile duct stricture demonstrates a circumferential lysis of collagen at the treatment site, while sparing damage to the normal duct, arteries and veins.

Example 6

Relief of Stenosis Due to Intimal Hyperplasia of a Synthetic Hemodialysis Graft Standard, untapered 5 mm diameter polytetrafluoroethylene (PFTE) loop grafts were interposed between the femoral artery and the femoral vein in the hind limbs of 25-35 kg dogs, as described previously (Trerotola, *J. Vascular and Interventional Radiology* (1995) 6:387-96). An end-to-end configuration had been selected to facilitate optimal positioning of the catheter drug delivery balloon during treatment of a stenosis. Standard, cut-film angiography is performed one week after surgery to assess the arterial inflow, the artery-graft anastomosis, the vein-graft anastomosis, and the venous outflow. After this, routine physical examination of the grafts will be carried out to screen for patency. Twenty weeks after surgery, standard, cut-film angiography is performed to assess the lumenal diameter of the grafts and their venous outflow. At this time, a stenosis due to intimal hyperplasia is seen in the venous outflow with an associated pressure gradient (Trerotola, *J. Vascular and Interventional Radiology* (1995) 6:387-96). Then, using the first animal, the therapy delivery catheter is deployed within a graft and 5000 ABC units of collagenase in 0.5 ml is infiltrated into the wall of the lesion at the venous outflow. The catheter is flushed and the contralateral lesion receives 1 ml of saline, delivered in an identical manner. Nearly all collagenase activity is extinguished after 1-2 days such that the grafts are re-examined with angiography after 3 days. Repeat measurements of lumenal diameter and invasive pressure measurements across the lesion are also taken. The animals are sacrificed and the grafts excised, pressure-fixed, and examined histologically. Assessments are made of the distal graft, the venous anastomosis, the mid-portion of the treated lesion, the lesion edge, and the normal vein downstream from the graft. Additional assessments of 1) cell type, morphology and number, 2) extent of extracellular matrix, 3) overall adventitial, medial, and intimal thickness, 4) extent of intimal hyperplasia, and 5) extent of endothelialization are made.

Example 7

Four dogs are used for a controlled study of collagenase treatment. Bilateral grafts are created as described previously and standard, cut-film angiography is performed one week after surgery to access the arterial inflow, the artery-graft anastomosis, the vein-graft anastomosis, and the venous outflow. After this, routine physical examination of the grafts is carried out to screen for patency. Then, twenty weeks after surgery, standard, cut-film angiography is performed to assess the lumenal diameter of the grafts and their venous outflow. An obvious stenosis due to intimal hyperplasia is usually seen in the venous outflow with an associated pressure gradient (Trerotola, *J. Vascular and Interventional Radiology* (1995) 6:387-96). The Infiltrator catheter is then deployed within the lesion and the selected dose of collagenase is infiltrated into the wall of the lesion. The contralateral, control graft is treated in an identical manner, except that saline is delivered instead of collagenase. Three days after treatment, the grafts are restudied with angiography and invasive pressure measurements to determine the acute effects of collagenase treatment. Changes in lumenal diameter and pressure gradients are calculated for both the collagenase-treated group and the saline-treated group and ten days after collagenase treatment, the grafts are studied a final time. The animals are sacrificed and the grafts are excised, pressure-fixed, and examined histologically, as described above.

The invention has been described in detail with reference to preferred embodiments thereof. However, it will be appreciated that those skilled in the art, upon consideration of this disclosure, may make modifications and improvements within the spirit and scope of the invention as set forth in the following claims.

What is claimed is:

1. A kit for enlarging the diameter of an artery in a human subject, said artery having a lumen, the kit comprising:
   (a) a catheter configured for injecting a pharmaceutical composition directly into a selected segment of the wall of the artery; and
   (b) a pharmaceutical composition suitable for administration to the human subject comprising an elastase,
   wherein said elastase is present in a dose sufficient to enlarge the diameter of the artery and the diameter of the lumen of the artery when administered via the catheter to the wall of the artery in the human subject.

2. A kit for enlarging the diameter of a vein in a human subject, said vein having a lumen, the kit comprising:
   (a) a catheter configured for injecting a pharmaceutical composition directly into a selected segment of the wall of the vein; and
   (b) a pharmaceutical composition suitable for administration to the human subject comprising an elastase,
   wherein said elastase is present in a dose sufficient to enlarge the diameter of the vein and the diameter of the lumen of the vein when administered via the catheter to the wall of the vein in the human subject.

3. The kit of claim 1 or 2, wherein the catheter comprises a channel for delivery of said pharmaceutical composition.

4. The kit of claim 1 or 2, further comprising a delivery device containing the pharmaceutical composition wherein the delivery device is connected to the catheter for injecting the pharmaceutical composition directly into the wall of said artery or vein.

5. The kit of claim 4, wherein the delivery device is a syringe.

6. The kit of claim 1 or 2, wherein the catheter comprises at least one injector port configured for injecting the pharmaceutical composition directly into the wall of the artery or vein.

7. The kit of claim 6, wherein said at least one injector port is mounted on the surface of an inflatable balloon.

8. The kit of claim 1 or 2, wherein the elastase is a pancreatic elastase.

9. The kit of claim 1 or 2, wherein the composition does not comprise a collagenase.

10. The kit of claim 1 or 2, wherein the catheter comprises a plurality of injector ports configured for injecting the pharmaceutical composition directly into the wall of the artery or vein.

11. The kit of claim 10, wherein said injector ports can be extended so as to enter the wall of the artery or vein.

12. The kit of claim 10, wherein said injector ports are mounted on the surface of one or more inflatable balloons.

13. The kit of claim 1 or 2, wherein the catheter and the pharmaceutical composition are packaged in combination.

14. The kit of claim 1 or 2, wherein the catheter comprises a reservoir suitable for containing the pharmaceutical composition.

* * * * *